(12) United States Patent
Pala

(10) Patent No.: US 9,358,344 B2
(45) Date of Patent: Jun. 7, 2016

(54) INJECTION DEVICE WITH PLURAL DOSAGE SETTING WINDOWS

(75) Inventor: Trivikrama Pala, Wayne, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 126 days.

(21) Appl. No.: 14/118,193

(22) PCT Filed: May 19, 2011

(86) PCT No.: PCT/US2011/000898
§ 371 (c)(1),
(2), (4) Date: Nov. 15, 2013

(87) PCT Pub. No.: WO2012/158138
PCT Pub. Date: Nov. 22, 2012

(65) Prior Publication Data
US 2014/0094765 A1    Apr. 3, 2014

(51) Int. Cl.
*A61M 5/315* (2006.01)
*A61M 5/24* (2006.01)
*A61M 5/31* (2006.01)

(52) U.S. Cl.
CPC ....... *A61M 5/31573* (2013.01); *A61M 5/31525* (2013.01); *A61M 5/31535* (2013.01); *A61M 5/31541* (2013.01); *A61M 5/31551* (2013.01); *A61M 5/31561* (2013.01); *A61M 5/31585* (2013.01); *A61M 2005/2407* (2013.01); *A61M 2005/3126* (2013.01); *A61M 2205/581* (2013.01); *A61M 2205/582* (2013.01); *A61M 2205/583* (2013.01)

(58) Field of Classification Search
CPC ..................... A61M 5/31541; A61M 5/31551; A61M 5/31561; A61M 5/31525; A61M 5/31535; A61M 5/31585; A61M 5/31568; A61M 5/31573; A61M 5/3157; A61M 2005/3126; A61M 2205/583; A61M 2205/584; A61M 2205/585
See application file for complete search history.

(56) References Cited

U.S. PATENT DOCUMENTS

| 2,279,858 | A | 4/1942 | Breitling et al. |
| 6,086,567 | A | 7/2000 | Kirchhofer et al. |
| 6,221,053 | B1 * | 4/2001 | Walters et al. ................ 604/211 |
| 7,766,188 | B2 | 8/2010 | Pocock et al. |
| 8,372,042 | B2 * | 2/2013 | Wieselblad ................... 604/186 |
| 8,444,606 | B2 | 5/2013 | Radmer et al. |
| 8,512,296 | B2 * | 8/2013 | Gabriel et al. ................ 604/207 |
| 8,721,601 | B2 * | 5/2014 | Burren et al. ................. 604/211 |

(Continued)

FOREIGN PATENT DOCUMENTS

| GB | 789629 A | 1/1958 |
| JP | 2000-182135 | 6/2000 |

(Continued)

*Primary Examiner* — Andrew Gilbert
(74) *Attorney, Agent, or Firm* — Dickinson Wright PLLC

(57) ABSTRACT

An injection device (100) including a body (108, 332) for containing and dispensing a medicament, the body (108, 332) having a plurality of dosage indicator windows (120, 124; 336, 340, 344) for indicating a desired dosage of medicament, and a dose set sleeve (192, 326, 352) rotatably connected with the body (108, 332) for setting the desired dosage, the dose set sleeve (192, 326, 352) having a plurality of dosage numbers (196, 348) disposed thereon. Upon rotating the dose set sleeve (192, 326, 352) to set the desired dosage, the dosage numbers (196, 348) are consecutively visible through alternating ones of the plurality of dosage indicator windows (120, 124; 336, 340, 344).

20 Claims, 17 Drawing Sheets

(56) References Cited

U.S. PATENT DOCUMENTS

| | | | |
|---|---|---|---|
| 2008/0173669 A1* | 7/2008 | Pocock | A61M 15/0065 222/36 |
| 2008/0269688 A1* | 10/2008 | Colucci | A61M 5/31551 604/189 |
| 2009/0264828 A1 | 10/2009 | Dette et al. | |
| 2009/0293870 A1* | 12/2009 | Brunnberg | A61M 15/0076 128/203.12 |
| 2010/0168677 A1* | 7/2010 | Gabriel et al. | 604/189 |
| 2010/0274198 A1* | 10/2010 | Bechtold | 604/189 |
| 2011/0015576 A1 | 1/2011 | Plumptre et al. | |
| 2011/0276006 A1 | 11/2011 | Matthias et al. | |
| 2011/0313365 A1* | 12/2011 | Wieselblad | A61M 5/31525 604/207 |
| 2012/0010575 A1 | 1/2012 | Jones et al. | |
| 2012/0037530 A1* | 2/2012 | Boyd et al. | 206/459.5 |
| 2013/0016105 A1* | 1/2013 | Raab | A61M 5/31551 345/440 |
| 2014/0046268 A1* | 2/2014 | Quinn et al. | 604/209 |
| 2014/0163477 A1* | 6/2014 | Quinn et al. | 604/207 |

FOREIGN PATENT DOCUMENTS

| | | |
|---|---|---|
| JP | 2000-070368 | 7/2000 |
| JP | 2003-033434 | 4/2003 |
| WO | 2009141003 A1 | 11/2009 |
| WO | 2009141067 A1 | 11/2009 |
| WO | WO2009141003 A1 * | 11/2009 |
| WO | 2010084164 A1 | 7/2010 |
| WO | 2010097125 A1 | 9/2010 |
| WO | WO2010097125 A1 * | 9/2010 |
| WO | 2011067267 A1 | 6/2011 |

* cited by examiner

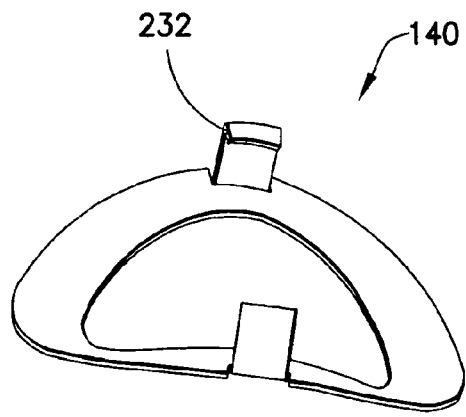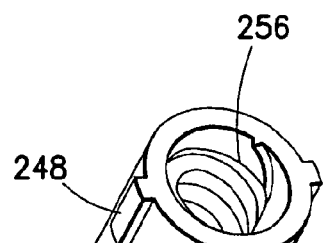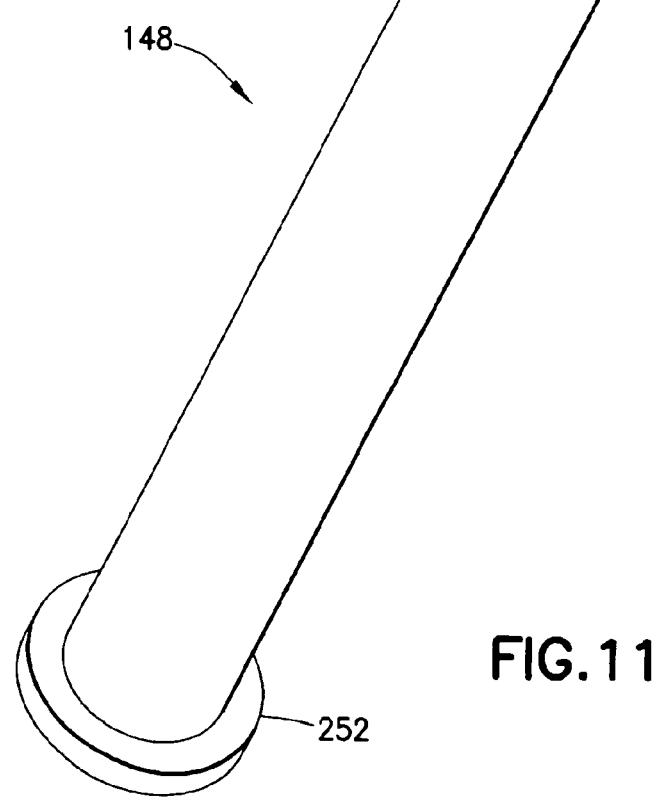
FIG.10
FIG.11

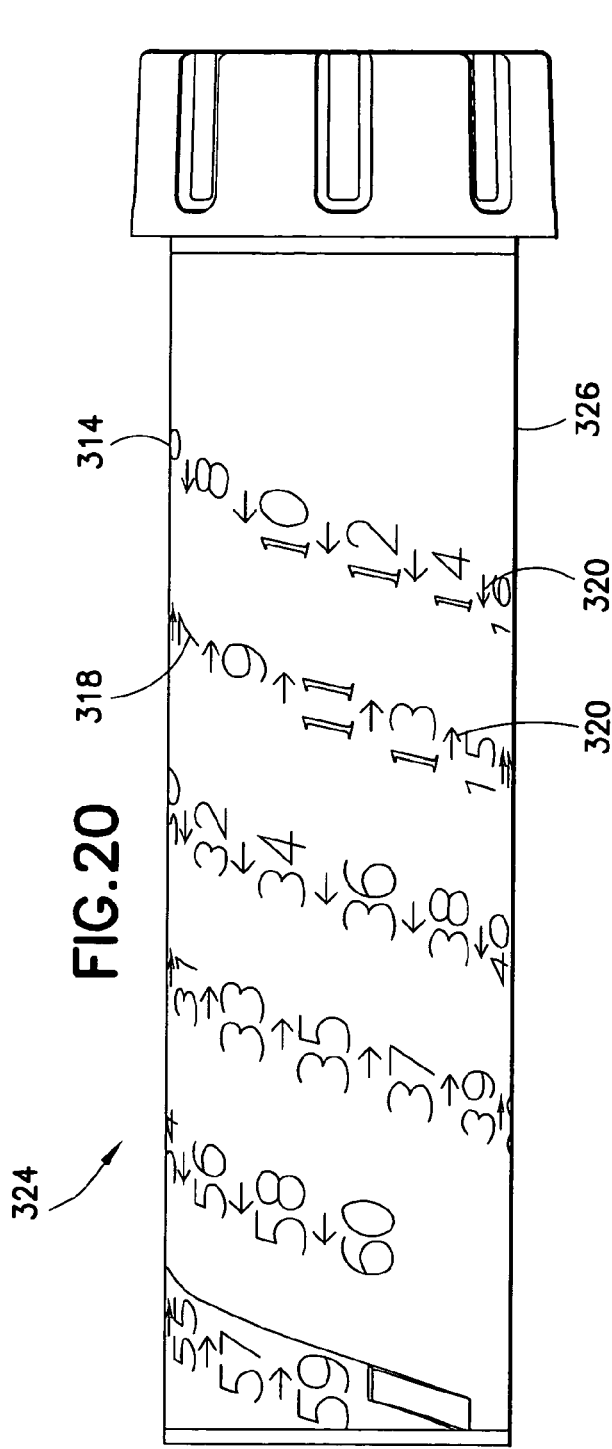
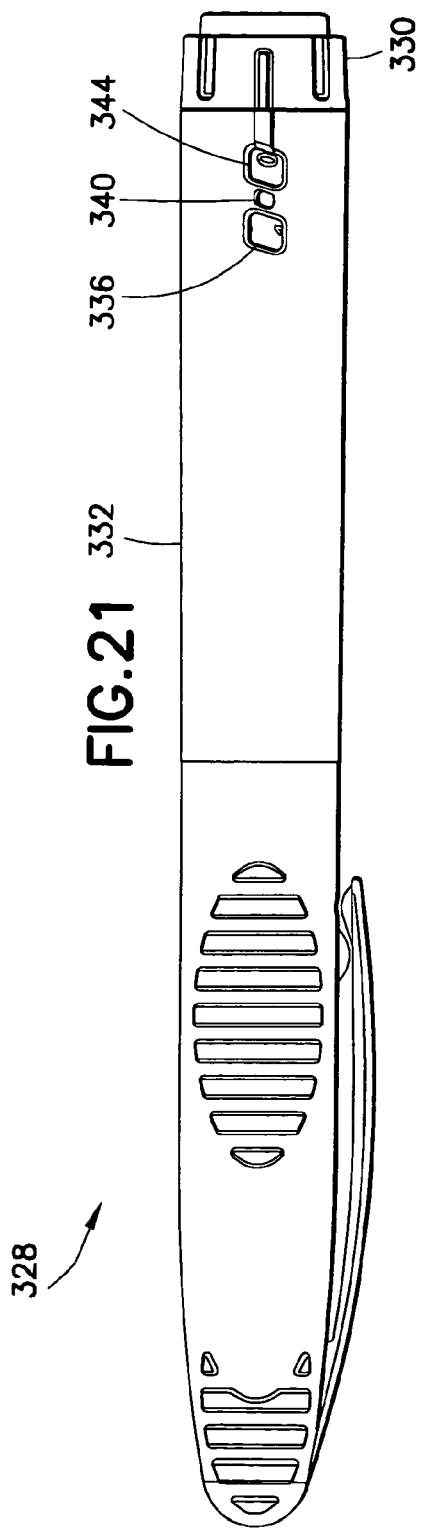

INJECTION DEVICE WITH PLURAL DOSAGE SETTING WINDOWS

FIELD OF THE INVENTION

The present invention relates generally to an injection device for dispensing a medicament, and more particularly to an injection device having a plurality of windows for setting a dose.

BACKGROUND OF THE INVENTION

Various injection devices are known in the art. Many such injection devices have a single window with a pointer for setting the dosage to be injected. It can be difficult for a user to match a scale line of a dose setting mechanism to the pointer, particularly if the user's vision is impaired. Further, in many such injection devices the scale line includes only even numbers, thus requiring interpolation by the user. In addition, the numbers and scale lines are small, adding to the difficulty for the user. Moreover, in such devices, the currently desired dosage number and other adjacent dosage numbers may be visible in the window of the device at the same time, thereby potentially confusing the user. Accordingly, it is desirable for an injection device to make dosage setting easy for a user, to help ensure proper dosing of the injected medicament.

SUMMARY OF THE INVENTION

An aspect of the present invention is to provide an injection device in which dosage setting is simplified, particularly for visually impaired users.

The foregoing and/or other aspects of the present invention are achieved by providing an injection device, including a body for containing and dispensing a medicament, the body having a plurality of dosage indicator windows for indicating a desired dosage of medicament, and a dose set sleeve rotatably connected with the body for setting the desired dosage, the dose set sleeve having a plurality of dosage numbers disposed thereon in fixed relation with one another. Different dosage indicator windows display different ones of the dosage numbers.

The foregoing and/or other aspects of the present invention are also achieved by providing an injection device, including a body for containing and dispensing a medicament, the body having a plurality of dosage indicator windows for indicating a desired dosage of medicament, and a dose set sleeve rotatably connected with the body for setting the desired dosage, the dose set sleeve having a plurality of dosage numbers disposed thereon. Upon rotating the dose set sleeve to set the desired dosage, the dosage numbers are consecutively visible through alternating ones of the plurality of dosage indicator windows.

The foregoing and/or other aspects of the present invention are also achieved by providing a method of setting a dose for an injection device having a body and a dose set sleeve having a plurality of dosage numbers arrayed thereon. The method includes rotating the dose set sleeve to make the dosage numbers consecutively visible through alternating ones of a plurality of dosage indicator windows on the body.

Additional and/or other aspects and advantages of the present invention will be set forth in part in the description that follows and, in part, will be apparent from the description, or may be learned by practice of the invention.

BRIEF DESCRIPTION OF THE DRAWINGS

The above and/or other aspects and advantages of embodiments of the invention will be more readily appreciated from the following detailed description, taken in conjunction with the accompanying drawings, in which:

FIG. 10 is a perspective view of a wave clip of the device of FIG. 1;

FIG. 11 is a perspective view of a piston rod of the device of FIG. 1;

FIG. 20 is a perspective view of a DSK of the device of FIG. 19;

FIG. 21 is a perspective view of an injection device in accordance with another embodiment of the present invention;

DETAILED DESCRIPTION OF EXEMPLARY EMBODIMENTS

Figure 1:
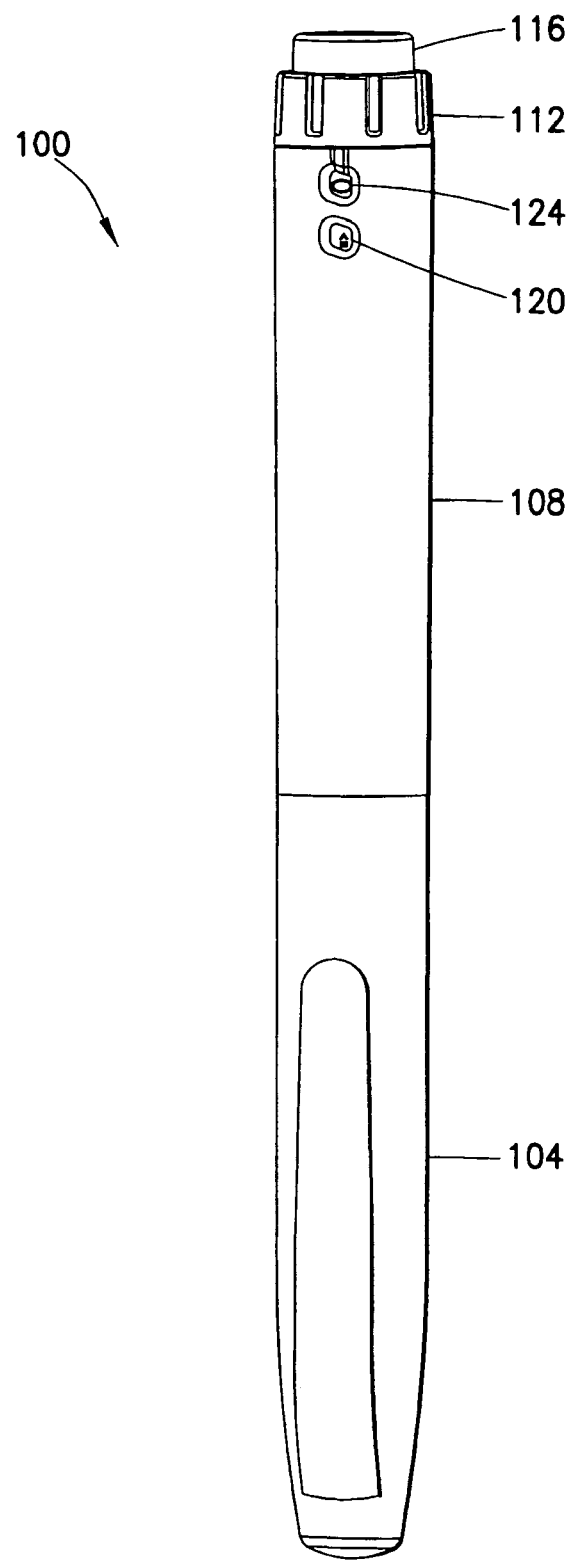
FIG. 1 is a perspective view of an injection device in accordance with an embodiment of the present invention.

Reference will now be made in detail to embodiments of the present invention, examples of which are illustrated in the accompanying drawings, wherein like reference numerals refer to the like elements throughout. The descriptions of these embodiments exemplify the present invention by referring to the drawings.

This specification refers to "distal," "forward" or "front" interchangeably and "proximal," "rear" or "back" interchangeably to refer to directions or ends of various components. Those terms are used for illustration and discussion purposes only. The particular arrangement of components and their directions of movement contained in the illustrated examples are not to be construed in a limiting sense.

FIG. 1 is a perspective view of an injection device 100 in accordance with an embodiment of the present invention. Injection device 100 includes a cap 104, a body or pen body 108, a dose setting knob (DSK) 112, and an injection button or button 116. According to one embodiment, the pen body 108 includes first and second dosage indicator windows 120 and 124 disposed at a proximal end thereof. As described in greater detail below, dosage numbers disposed on the sleeve (or dose setting sleeve) of the DSK 112 are visible through one of the dosage indicator windows 120 and 124 at a time. In other words, according to one embodiment, the dosage indicator windows 120 and 124 are used to set a current desired dosage and the dosage numbers become visible through the each of the dosage indicator windows 120 and 124, but are only visible through one of the dosage indicator windows at a time. That is, according to one embodiment, different dosage indicator windows display different ones of the dosage numbers. Put another way, according to one embodiment, the dosage numbers are consecutively visible in alternating ones of the dosage indicator windows.

Figure 2:
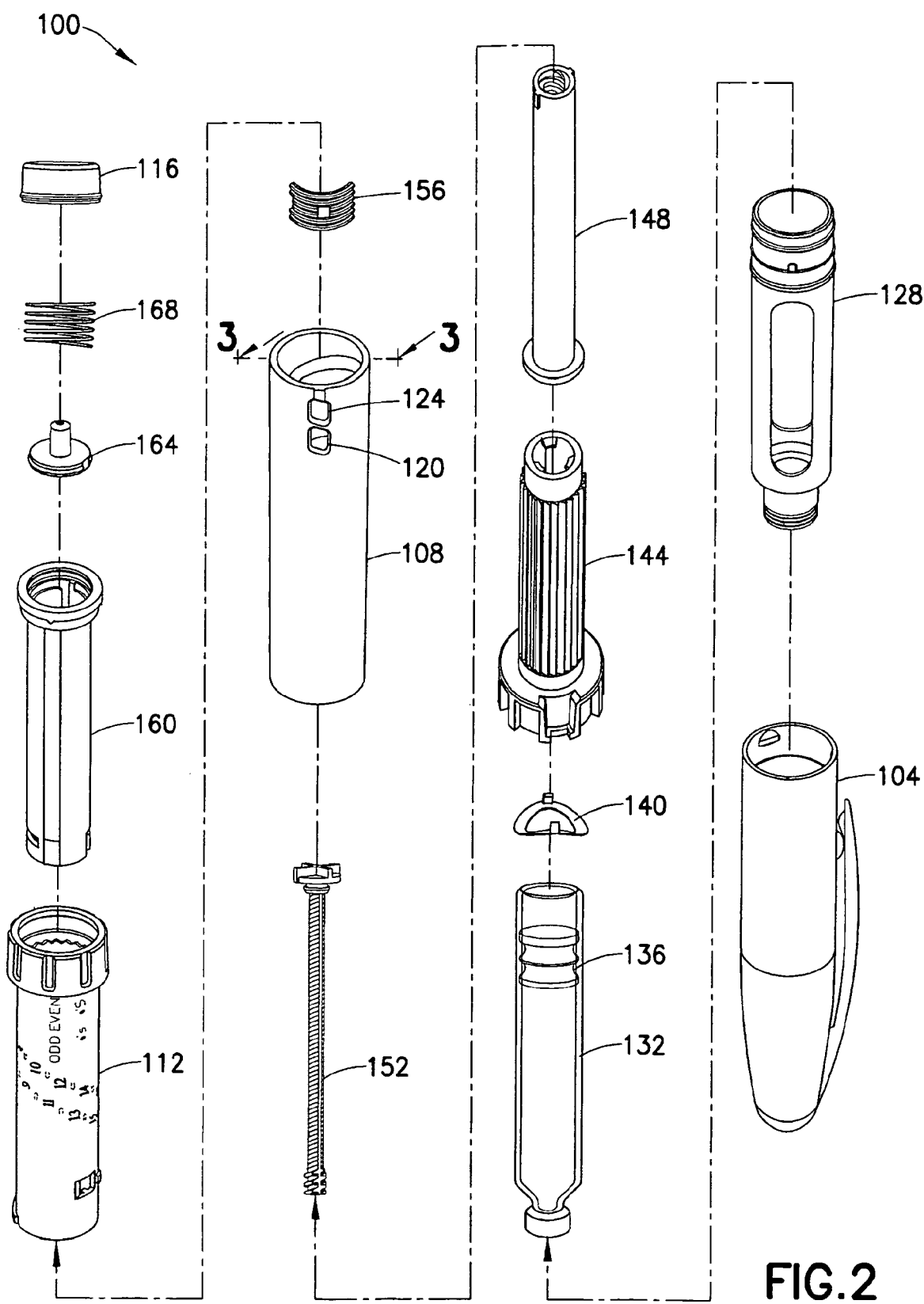
FIG. 2 is an exploded view of the device of FIG. 1.

FIG. 2 is an exploded perspective view of the injection device 100. In addition to the cap 104, the pen body 108, the DSK 112, and the injection button 116, the injection device 100 includes a cartridge holder 128 and a medicament cartridge 132 with a stopper 136 movably disposed therein. The injection device 100 also includes a wave clip or wave spring clip 140 for supporting the medicament cartridge 132 and biasing the medicament cartridge 132 distally, a brake tower 144, a piston rod 148, a lead screw 152, a dose stop 156, a setback 160, a setback bearing insert 164, and a clicking spring 168.

Figure 3:
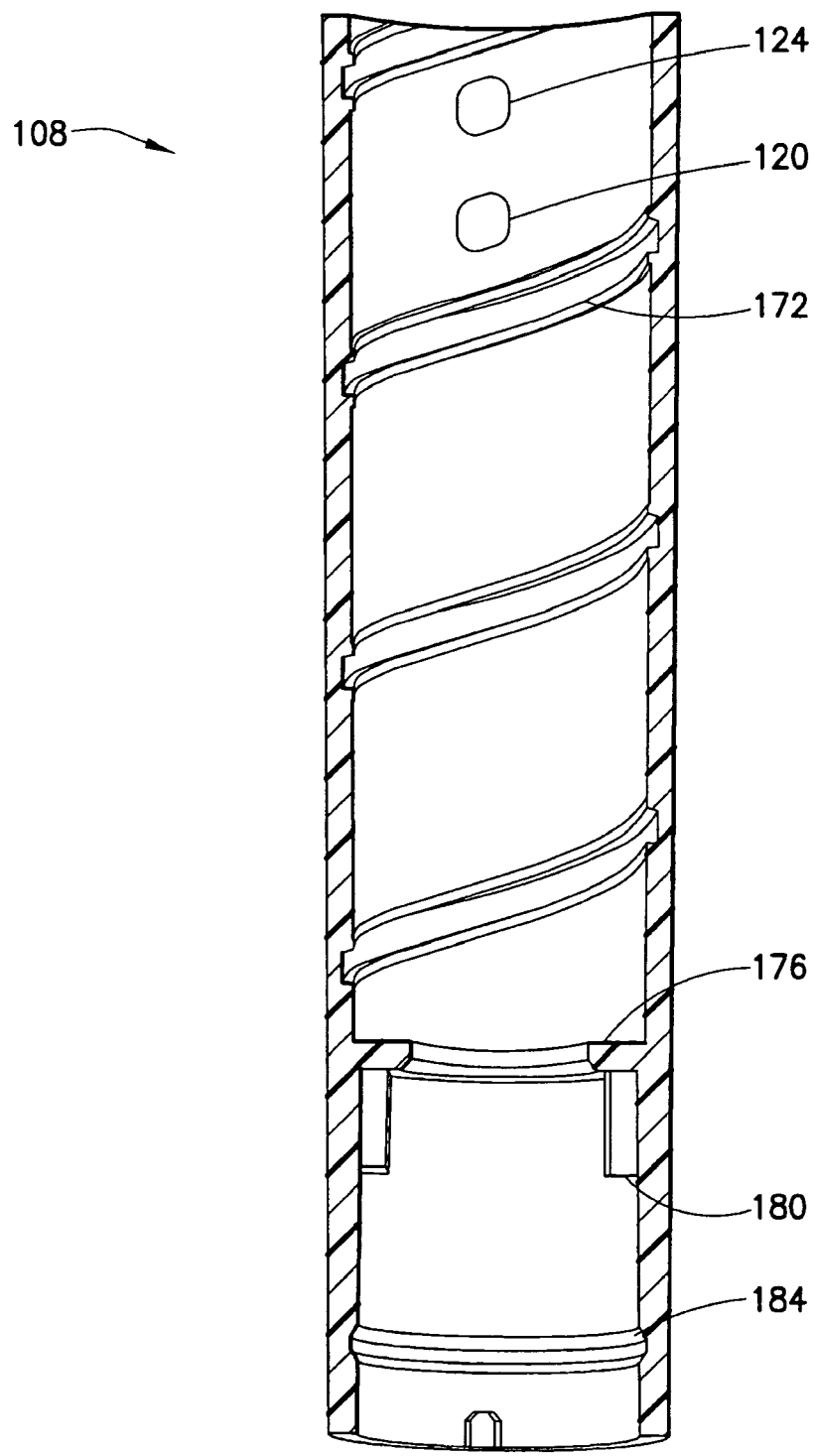
FIG. 3 is a cross-sectional view of a body of the device of FIG. 1 taken along line 3-3 of FIG. 2.
Figure 4:
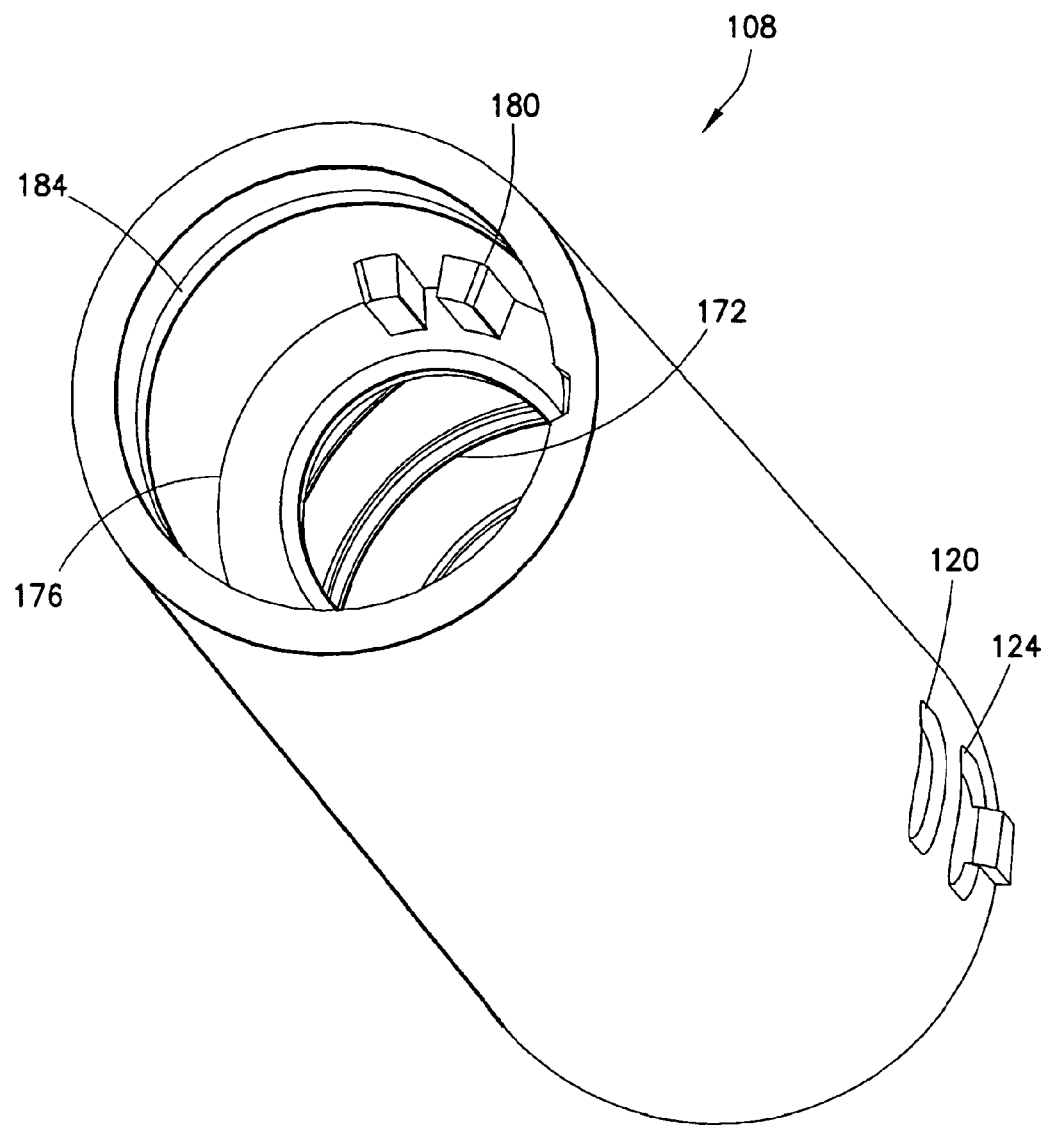
FIG. 4 is a perspective view of the body of FIG. 2.

FIG. 3 is a cross-sectional view of the body 108 taken along line 3-3 of FIG. 2 and FIG. 4 is a perspective view of the body 108. As shown in FIGS. 3 and 4, the body 108 includes a radially inward protruding wall 176 that, in conjunction with radially inward protruding bosses 180, registers the brake tower 144 relative to the body 108. Further, the body 108 includes a cartridge holder connecting thread 184 at a distal end thereof for engaging a corresponding thread on a proximal end of the cartridge holder 128 to connect the cartridge holder 128 and the body 8. The body 108 also includes a substantially helical internal thread 172 for guiding movement of the DSK 112 relative to the body 108.

Figure 5:
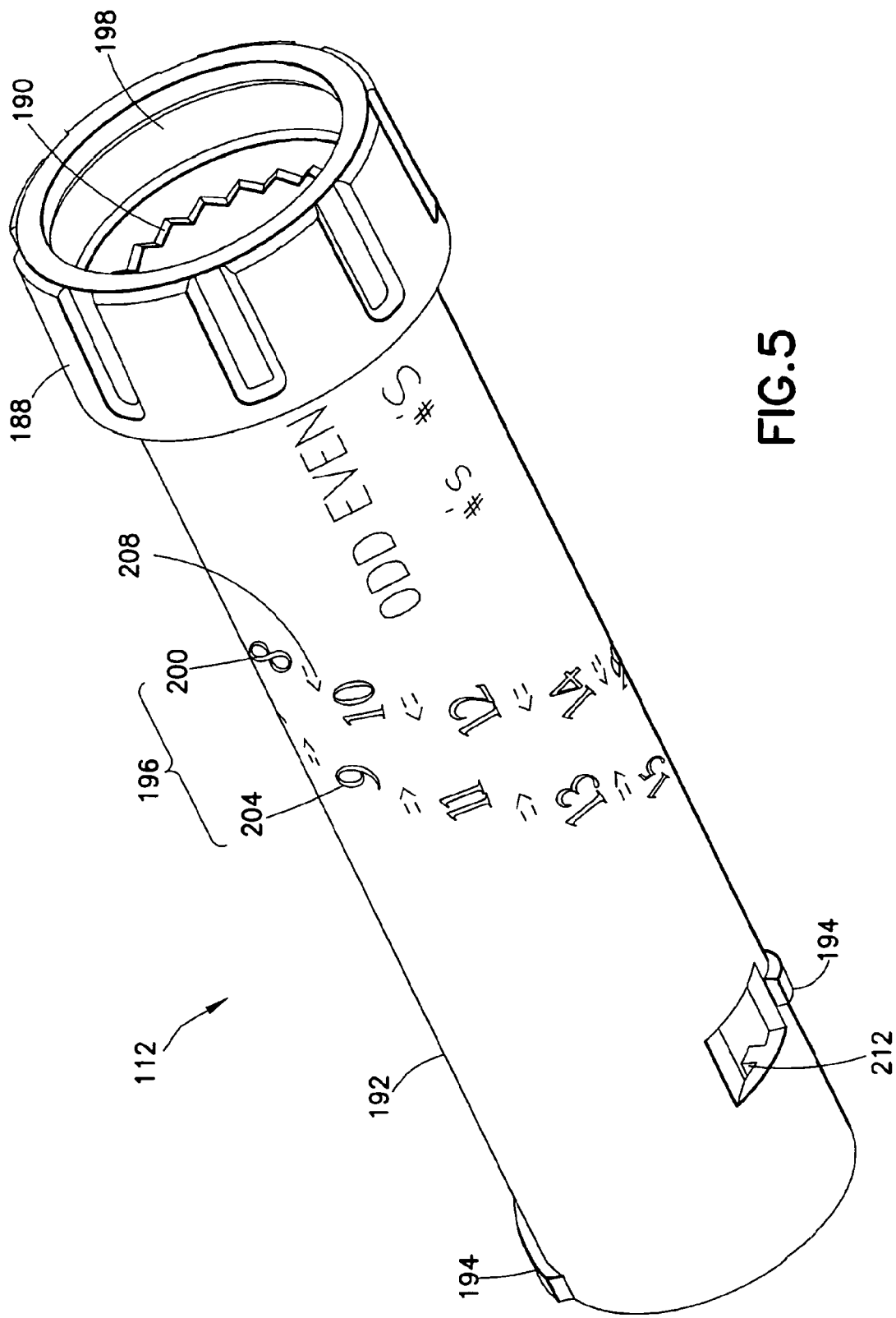
FIGS. 5 and 6 are perspective views of a dose setting knob (DSK) of the device of FIG. 1.
Figure 6:
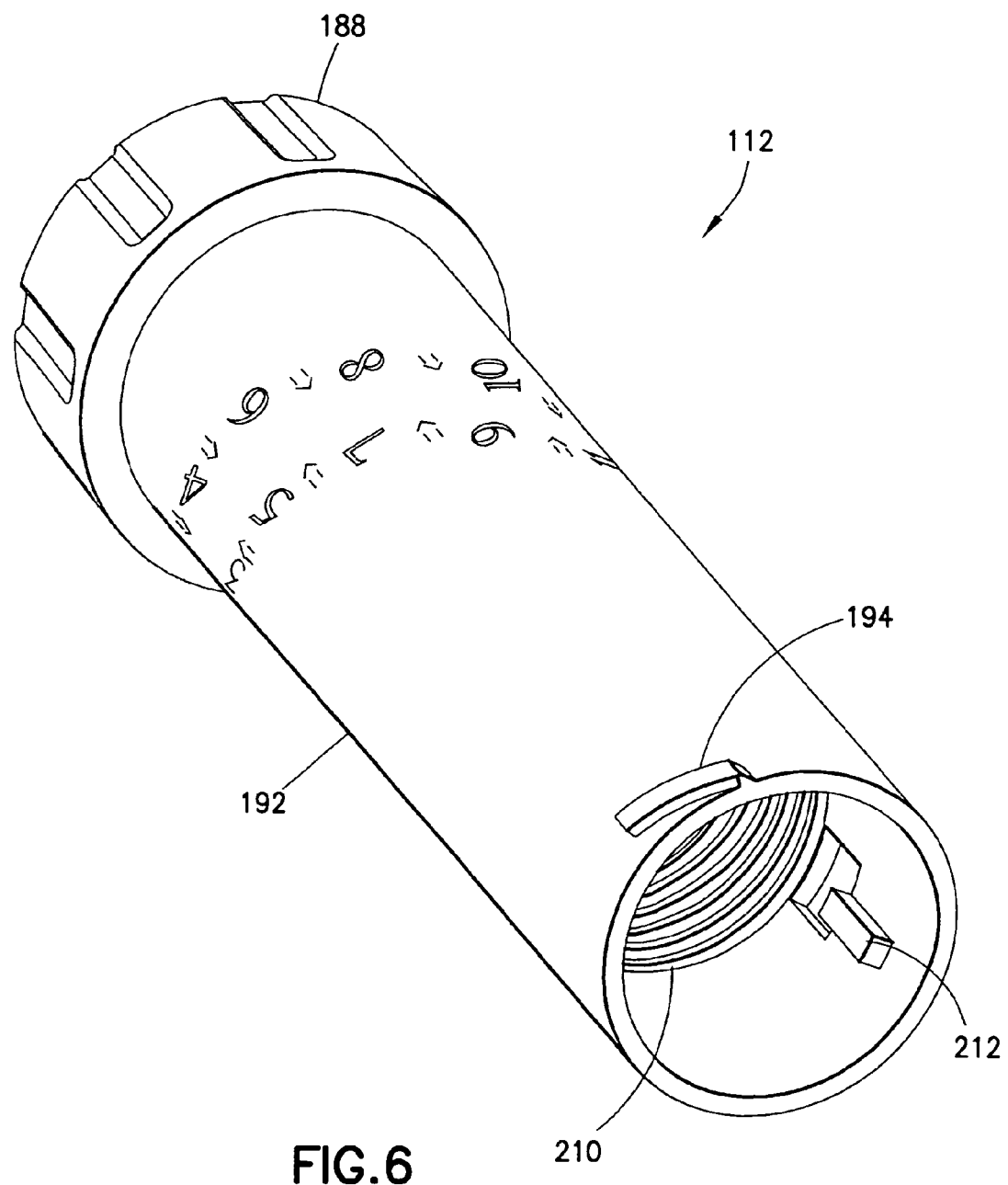

The DSK 112, shown in FIGS. 5 and 6, includes a gripping portion 188 and a sleeve portion or sleeve or dose setting sleeve 192 having a pair of keys 194 protruding radially outward therefrom. Internally, the gripping portion 188 has a plurality of teeth 190 for engaging the setback 160 and a button receiving portion 198 for receiving the button 116, as described in greater detail below. The keys 194 slidably engage the internal thread 172 of the body 108 to guide movement of the DSK 112 relative to the body 108. The sleeve 192 also has dosage numbers 196 arrayed thereon in fixed relation with one another in a pair of substantially helical patterns.

More specifically, a first helical pattern 200 includes even numbers and a second helical pattern 204 includes odd numbers. Non-number indicators 208 separate the even numbers of the first helical pattern 200 the odd numbers of the second helical pattern 204. According to one embodiment, the non-number indicators 208 are arrows 208 pointing toward the other helical pattern. For example, each arrow 208 in the first helical pattern 200 points toward a single odd number in the second helical pattern 204 and each arrow 208 in the second helical pattern 204 points toward a single even-numbered in the first helical pattern 200.

According to one embodiment, the even numbers of the first helical pattern 200 are visible through the second dosage indicator window 124 and the numbers of the second helical pattern 204 are visible through the first dosage indicator window 120. Further, according to one embodiment, a single one of the dosage numbers 196 is visible at a time. In other words, an even dosage number is visible through the second dosage indicator window 124, or an odd dosage number is visible through the first dosage indicator window 120. Put another way, a dosage number 196 is visible through a single one of the dosage indicator windows 120 and 124 at a time.

Figure 7:
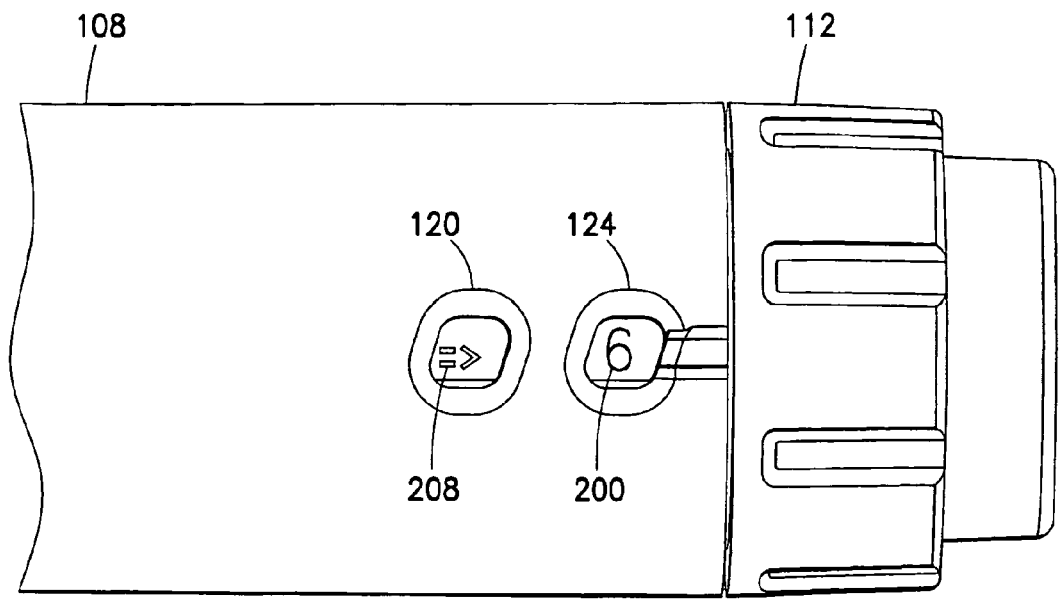
FIGS. 7 and 8 are partial perspective views of selected components of the device of FIG. 1.
Figure 8:
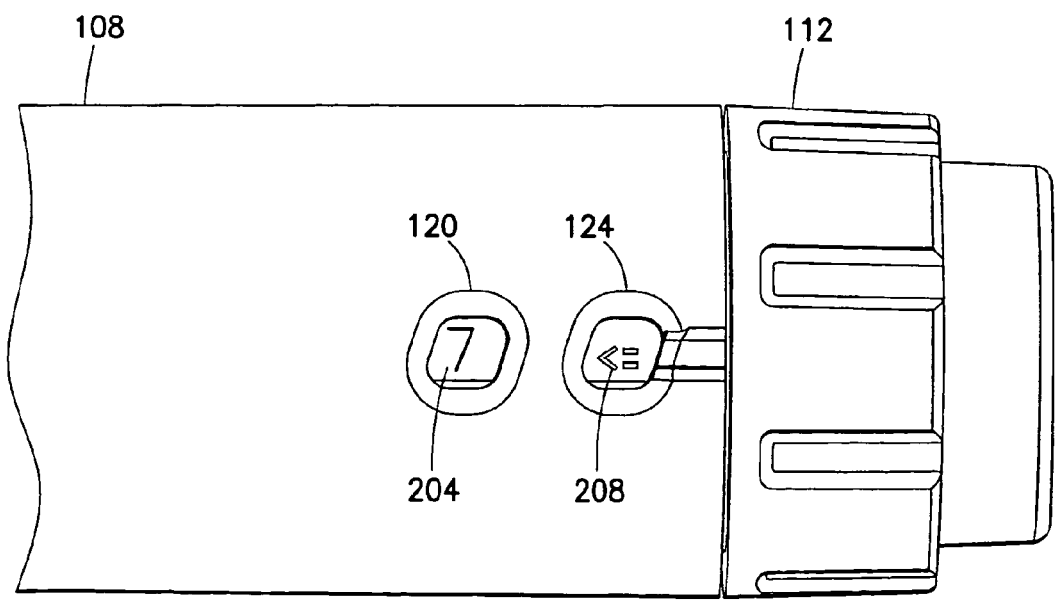

Moreover, according to one embodiment, when one of the dosage numbers 196 is visible through one of the dosage indicator windows, a non-number indicator 208 is visible through the other dosage indicator window pointing to the dosage number 196 visible through the dosage indicator window 120. More specifically, as shown in FIG. 7, when a dosage number 196 in the first helical pattern 200 (an even number) is visible through the second dosage indicator window 124, a non-number indicator 208 is visible through the first dosage indicator window 120. Similarly, as shown in FIG. 8, when for example when a dosage number 196 in the second helical pattern 204 (an odd number) is visible through the first dosage indicator window 120, a non-number indicator 208 is visible through the second dosage indicator window 124.

In addition, as described in greater detail below, the DSK 112 also has an internal dose stop thread 210 and a radially inward protruding dose stop blocker 212 for defining an end-of-dose condition in conjunction with the dose stop 156 and the setback 160. Further, according to one embodiment, the first and second dosage indicator windows 120 and 124 each include a magnifying lens for magnifying the dosage numbers to aid visually impaired users.

Figure 9:
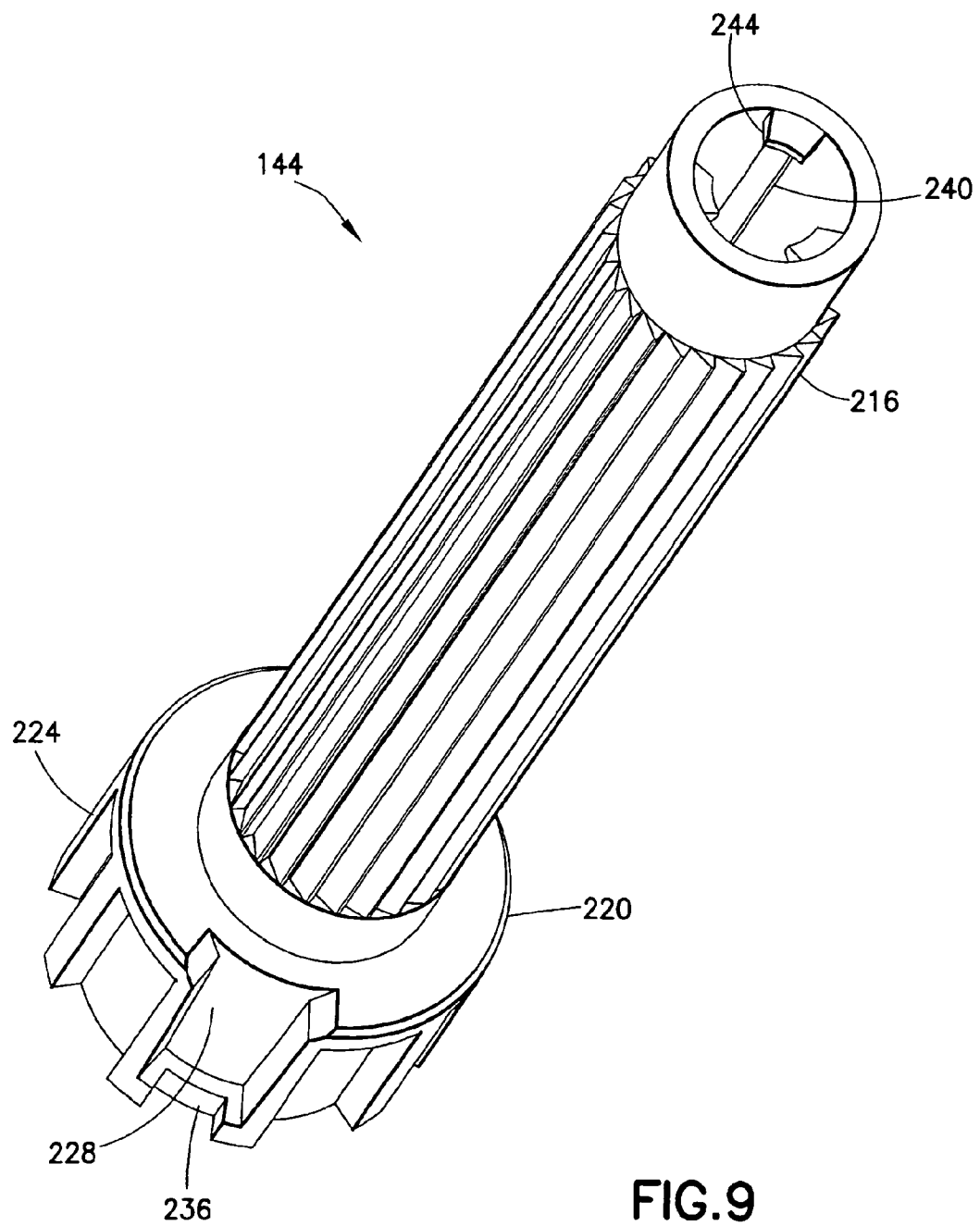
FIG. 9 is a perspective view of a brake tower of the device of FIG. 1.

As shown in FIG. 9, the brake tower 144 includes a plurality of ratchet teeth 216 disposed on a proximal portion thereof and a base portion 220 disposed at a distal end thereof. The base portion 220 includes a plurality of fins 224 and a pair of recessed portions 228. The recessed portions 228 engage the bosses 180 of the body 108 and the proximal surface of the base portion 220 registers against the wall 176 of the body 108 when the brake tower 144 is inserted into the distal end of the body 108. Further, arms 232 of the wave clip 140 (FIG. 10) engage recesses 236 of the base portion 220 to secure the wave clip 140 to the brake tower 144. The interior of the brake tower 144 has a pair of axial piston rod grooves 240 for guiding movement of the piston rod 148, and three limiters 244 for limiting proximal displacement of the piston rod 148.

The piston rod 148, shown in FIG. 11, includes a pair of piston rod keys 248 at a proximal end thereof for engaging the piston rod grooves 240 of the brake tower 144. The piston rod grooves 240 constrain displacement of the piston rod 148 to be axial relative to the brake tower 144. In addition, the piston rod 148 has a driving flange 252 disposed at a distal end thereof for engaging the stopper 136, to displace the stopper 136 relative to the medicament cartridge 132. Further, the interior of the piston rod 148 has a helical thread 256 for engaging the lead screw 152.

Figure 12:
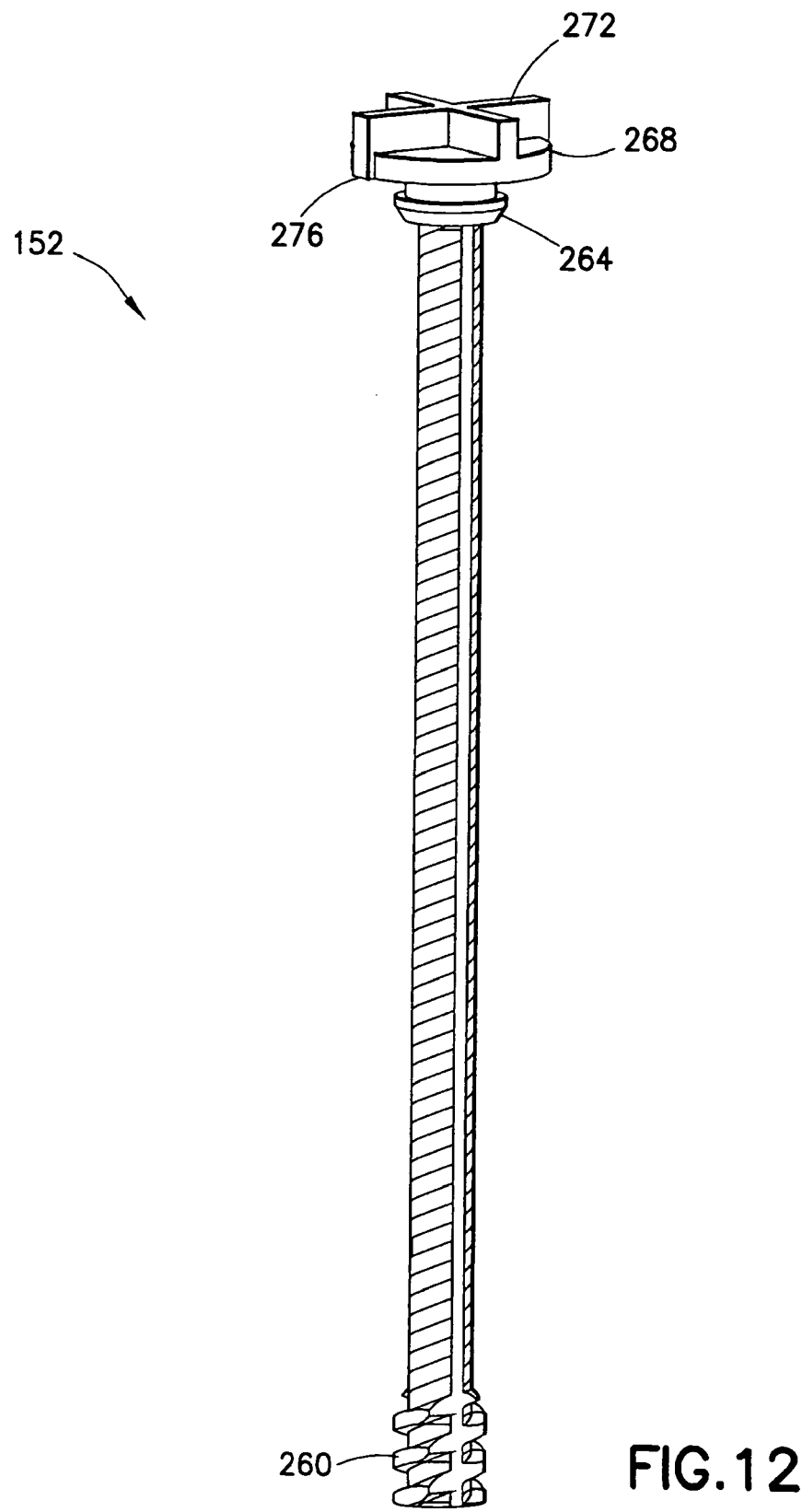
FIG. 12 is a perspective view of a lead screw of the device of FIG. 1.

As shown in FIG. 12, the lead screw 152 includes a piston rod thread portion 260 for engaging the thread 256 of the piston rod 148. An engaging portion 264 connects the lead screw 152 to the brake tower 144, for example, by a snap fit, thereby permitting rotation of the lead screw 152 relative to the brake tower 144 but preventing axial displacement of the lead screw 152 relative to the brake tower 144. Additionally, a substantially cylindrical proximal portion 268 has a raised structure 272 disposed thereon. According to one embodiment, the raised structure 272 has a cross or plus-sign shape. Two of the arms of the raised structure 272 extend radially beyond the perimeter of the proximal portion to form a pair of setback keys 276 that slidably engage an axial groove or keyway 280 in the setback 160. Interaction between the setback keys 276 and the keyways 280 constrain displacement of the setback 160 relative to the lead screw 152 to be substantially axial.

Figure 13:
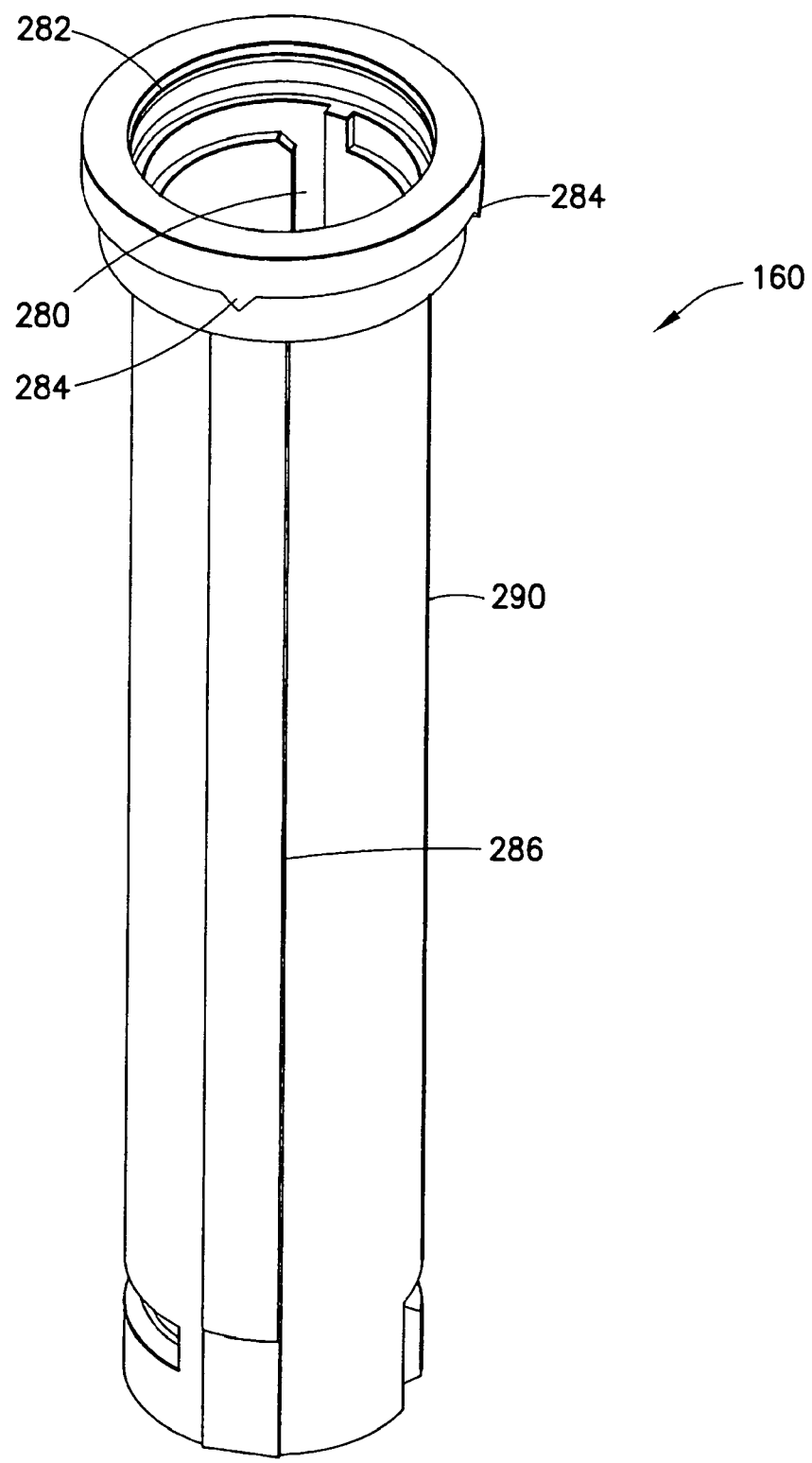
FIGS. 13 and 14 are perspective views of opposing ends of a setback of the device of FIG. 1.
Figure 14:
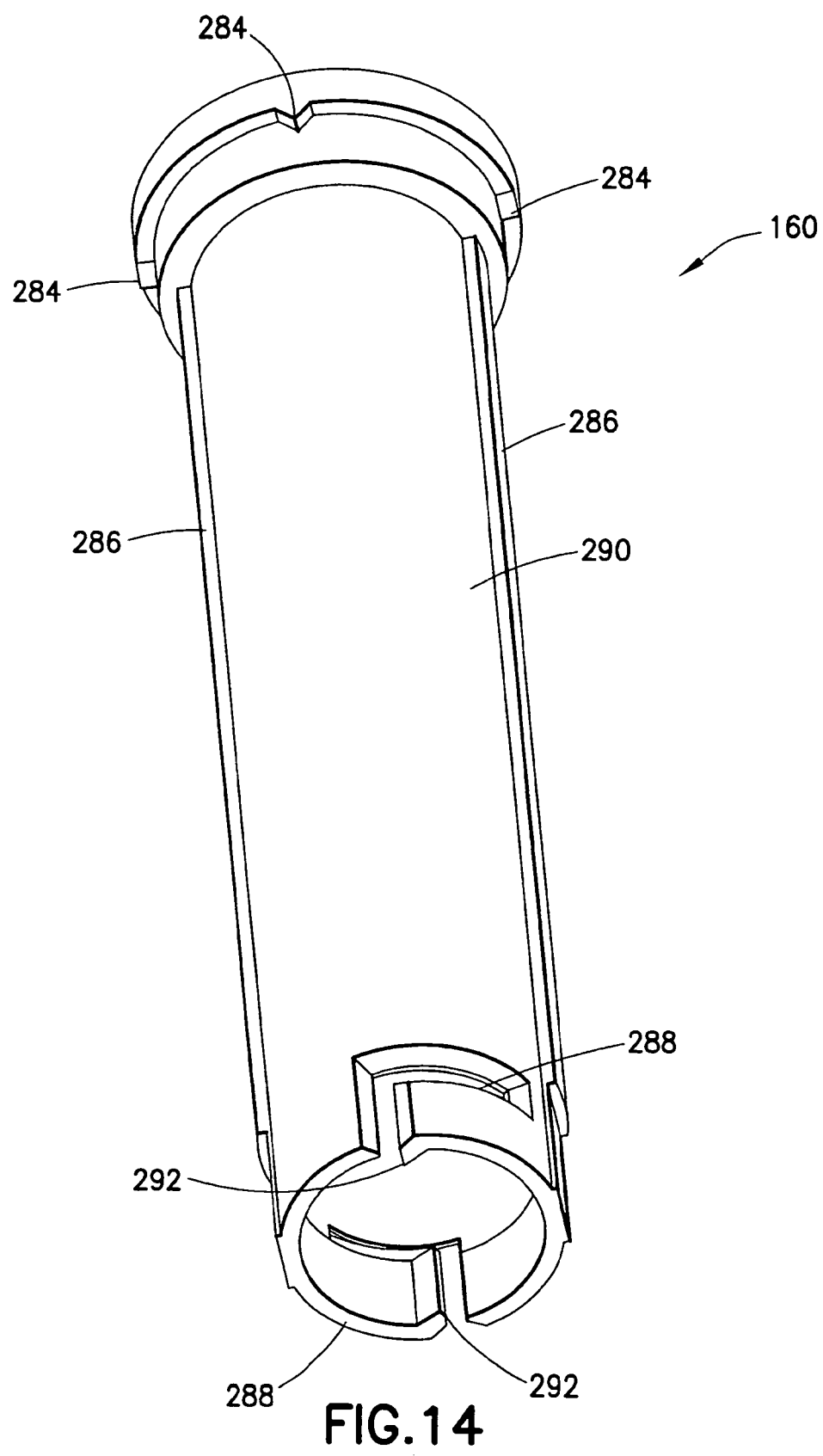

FIGS. 13 and 14 respectively illustrate distal and proximal ends of the setback 160. In addition to the axial groove or keyway 280 described previously, the setback 160 has a receiving portion 282 for receiving the setback bearing insert 164, for example, with a snap fit. The setback 160 also includes a plurality of DSK teeth 284, which, as described in greater detail below, engage the teeth 190 of the DSK 112. Further, as described in greater detail below, the setback 160 includes a pair of dose stop ridges 286 that engage lateral ends of the dose stop 156. The area between the dose stop ridges 286 defines a sliding surface 290 on which the dose stop 156 slides.

As shown in FIG. 14, the setback 160 also includes a pair of cantilevered arms 288, on which a respective pair of brake tower teeth 292 protrude radially inward. In conjunction with the ratchet teeth 216 of the brake tower 144 (FIG. 9), the cantilevered arms 288 and the brake tower teeth 292 permit one-way rotation of the setback 160 relative to the brake tower 144. Further, the interaction between the cantilevered arms 288, the brake teeth 292, and the ratchet teeth 216 permits axial displacement of the setback 160 relative to the brake tower 144.

Figure 15:
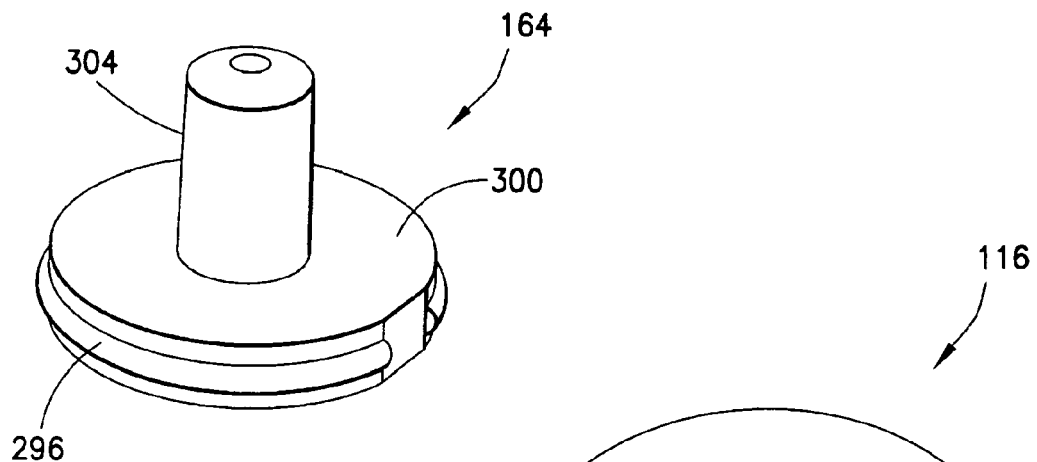
FIG. 15 is a perspective view of a setback bearing insert of the device of FIG. 1.
Figure 16:
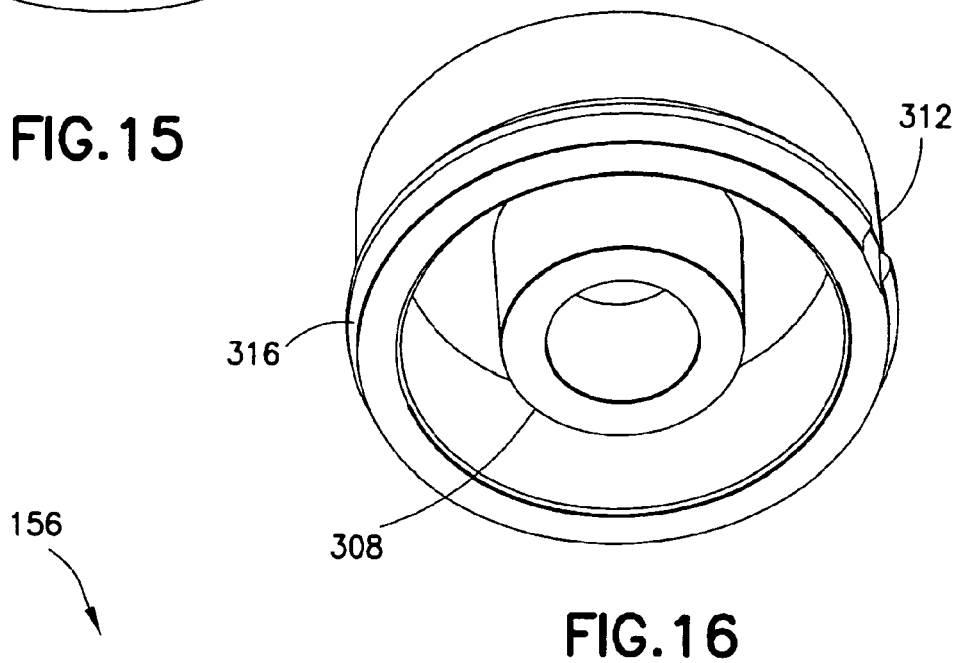
FIG. 16 is a perspective view of an injection button of the device of FIG. 1.

The setback bearing insert 164, shown in FIG. 15, includes an engaging portion 296 received in the receiving portion 282 of the setback 160, a bearing surface 300 against which clicking spring 168 bears, and a post 304 extending proximally from the bearing surface 300. The post 304 contacts an internal surface of the injection button 116, which is shown in FIG. 16. The injection button 116 includes a substantially cylindrical internal wall 308 proximally extending in an interior thereof. The post 304 fits into the interior of the internal wall 308 and a space between the internal wall 308 and an external wall 312 of the button 116 houses the spring, which bears both on the bearing surface 300 of the setback bearing insert 164 and an internal surface of the button 116. The button 116 also has an engagement portion 316 for engaging the button receiving portion 198 of the DSK 112, for example, with a snap fit. According to one embodiment, the button 116 is rotatable relative to the DSK 112.

During operation of the injection device 100, preferably after connecting a pen needle to the cartridge holder 128 and the medicament cartridge 132, a user sets a desired dosage by rotating the DSK 112 in a first direction. Because of the interaction between the keys 194 of the DSK 112 and the helical thread 172' of the body 108, rotation of the DSK 112 proximally displaces the DSK 112 and the setback 160. During this proximal displacement of the setback 160, the brake tower teeth 292 slide axially along the ratchet teeth 216 of the brake tower 144, which is secured to the body 108 via the bosses 180 and the recessed portions 228.

The engagement of the brake tower teeth 292 and the ratchet teeth 216 prevent rotation of the setback 160 in the first direction. In addition, the teeth 190 of the DSK 112 rotate past the DSK teeth 284 of the setback 160, thereby providing discrete rotational steps and feedback to the user, for example an audible click and/or tactile feedback. According to one embodiment, the discrete rotational steps correspond to an increase of one dosage number, for example, about 10° of rotation of the DSK 112. Thus, if an even dosage number is visible through the second dosage indicator window 124 (and the corresponding non-number indicator 208 is visible through the first dosage indicator window 120), as the user rotates the DSK 112 by a single discrete rotational step, an odd dosage number, one higher than the previously visible even number, becomes visible through the first dosage indicator window 120 (and the corresponding non-number indicator 208 becomes visible through the second dosage indicator window 124).

Subsequent to setting the desired dosage, the user presses the button 116 distally. Because of the interaction between the keys 194 of the DSK 112 and the helical thread 172 of the body 108, the distal displacement of the button 116 causes rotation of the DSK 112 in a second direction, opposite to the first direction. And because rotation of the setback 160 in the second direction is permitted by the engagement of the brake tower teeth 292 and the ratchet teeth 216, rotation of the DSK 112 in the second direction also rotates the setback 160 in the second direction.

Additionally, as previously noted, the engaging portion 264 of the lead screw 152 engages the brake tower 144 to permit rotation of the lead screw 152, but not axial displacement thereof relative to the brake tower 144. Thus, as the setback 160 rotates in the second direction, because of the keyed engagement of the setback key 276 and the groove 280, the lead screw rotates, thereby distally displacing the piston rod 148 because of the engagement of the piston rod thread 260 and the internal thread 256 and the engagement between the piston rod keys 248 and the piston rod grooves 240 of the brake tower 144. This distal displacement of the piston rod distally displaces the stopper 136 relative to the medicament cartridge 132 and expels medicament from the medicament cartridge 132 through the pen needle.

Figure 17:
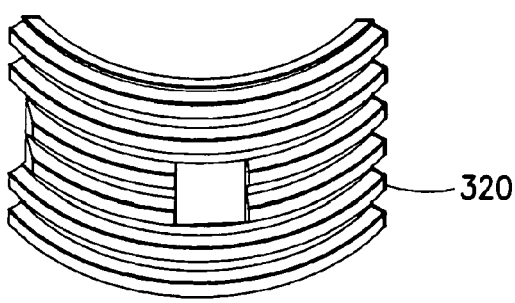
FIG. 17 is a perspective view of a dose stop of the device of FIG. 1.
Figure 18:
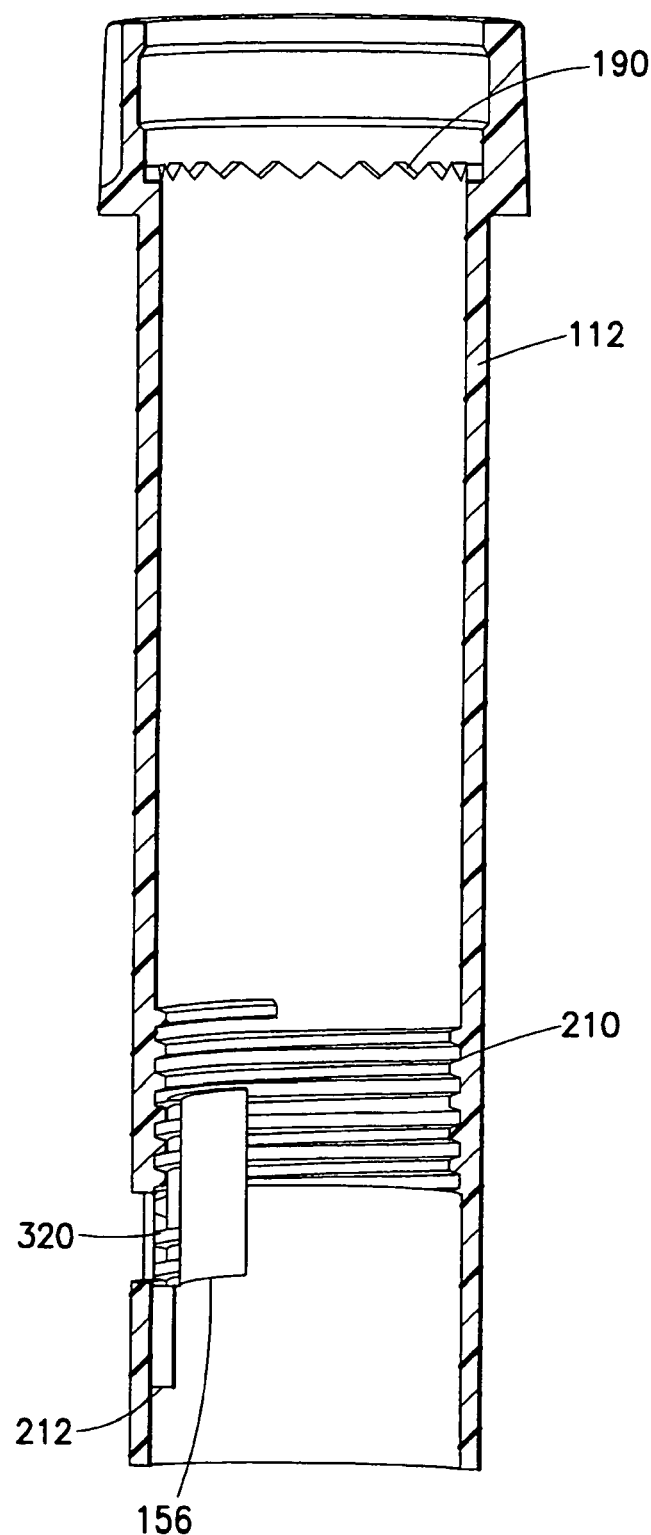
FIG. 18 is a cross-sectional view of the DSK of FIGS. 5 and 6 and the dose stop of FIG. 17.

FIG. 17 is a perspective view of a dose stop 156 and FIG. 18 is a cross-sectional view illustrating the interaction between the DSK 112 and the dose stop 156 at the occurrence of the end-of-dose condition. The dose stop 156 has DSK threads 320 that engage the dose stop thread 210 of the DSK 112. As noted previously, when the user rotates the DSK 112 in the first direction to set the desired dosage, the setback 160 displaces proximally but does not rotate in the first direction. Because of the engagement of the DSK threads 320 and the dose stop thread 210 and the engagement between the dose stop ridges 286 and the lateral ends of the dose stop 156, the rotation of the DSK 112 relative to the setback 160 causes the dose stop 156 to slide distally along the sliding surface 290 of the setback 160 and displace distally relative to the DSK 112. When the DSK 112 and the setback 160 rotate together in the second direction as the button 116 is pushed distally by the user, the dose stop 156 rotates along with the DSK 112 and the setback 160 and there is no relative displacement between the dose stop 156 and the DSK 112.

Upon sufficient cumulative rotation of the DSK 112 relative to the setback 160, the dose stop 156 contacts the dose stop blocker 212, which prevents further distal displacement of the dose stop 156 relative to the DSK 112. When this occurs, the DSK 112 can no longer rotate relative to the setback 160 (i.e., rotate in the first direction) because of the engagement of the DSK threads 320 and the dose stop thread 210 and the engagement between the dose stop ridges 286 and the lateral ends of the dose stop 156. This condition, as shown in FIG. 18, defines the end of medicament dosages available from the medicament cartridge 132. In other words, because the user can no longer rotate the DSK 112 in the first direction, no further desired dose can be set. In this state, however, the user can still depress the button 116 to expel the set dosage from the medicament cartridge 132.

Using the thread pitch of the DSK threads 320 and the dose stop thread 210, initial displacement of the dose stop 156 relative to the dose stop blocker 212 of the DSK 112 can be calculated to accommodate different volumes of medicament in the medicament cartridge 132. In other words, the initial axial distance and rotation of the dose stop relative to the dose stop blocker can be calculated. Put a different way, the amount of rotation of the DSK 112 to fully dispense a given volume of medicament (i.e., the number of unit doses in the medicament cartridge), as well as the thread pitch of the DSK threads 320 and the dose stop thread 210, determine how far the dose stop 156 is displaced relative to the dose stop blocker 212 during assembly of the injection device 100.

Conversely, a desired displacement of the dose stop during cumulative use of the injection device 100 can be used to calculate the thread pitch of DSK threads 320 and the dose stop thread 210. According to one embodiment, demarcations corresponding to different volumes of medicament are disposed on an interior of the DSK so that when a user replaces a medicament cartridge, the user can set the displacement of the dose stop 156 relative to the dose stop blocker 212 corresponding to the volume of medicament in the new medicament cartridge 132.

Figure 19:
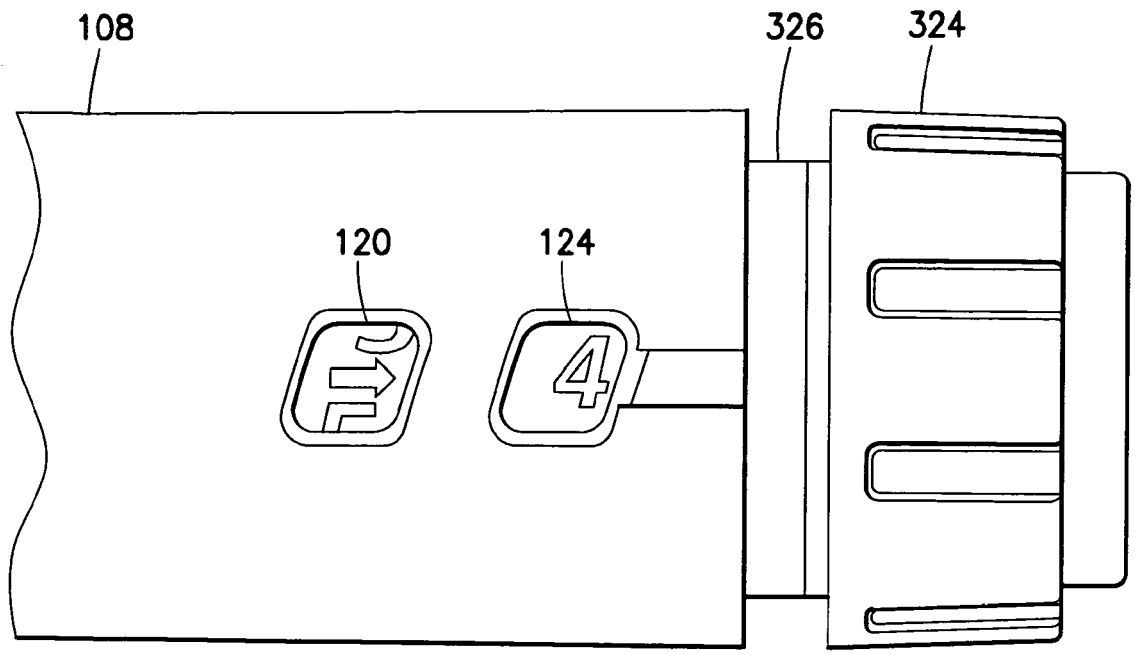
FIG. 19 is a partial perspective view of a body and DSK in accordance with another embodiment of the present invention.

The DSK 112 described previously (FIGS. 5 and 6) includes 16 discrete dose settings. In accordance with another embodiment of the present invention, as shown in FIGS. 19 and 20, if it is desired to have a smaller discrete dosage unit (or discrete rotational step), the even and odd dosage numbers 314 and 318 (as well as the non-number indicators 320) on a sleeve 326 of a DSK 324 can be placed closer together in their respective helical patterns. Correspondingly, the number of teeth disposed at the proximal end of the DSK 324 that interact with the DSK teeth 284 of the setback 160 also increase. For example, the discrete rotational steps may be, for example, about 5° of rotation of the DSK 324. Further, by decreasing the spacing between dosage numbers, even if there is not a corresponding increase in the number of teeth at the proximal end of the DSK 324, a larger font can be employed, thereby making use of the device easier for people with impaired vision.

Figure 22:
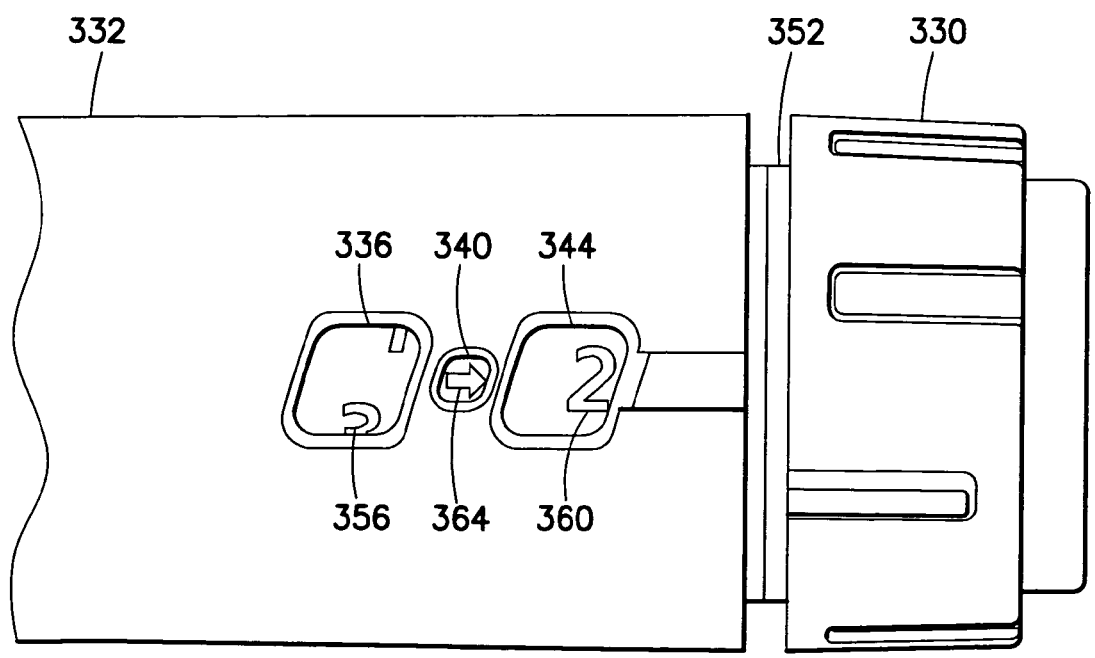
FIG. 22 is a partial perspective view of the device of FIG. 21.
Figure 23:
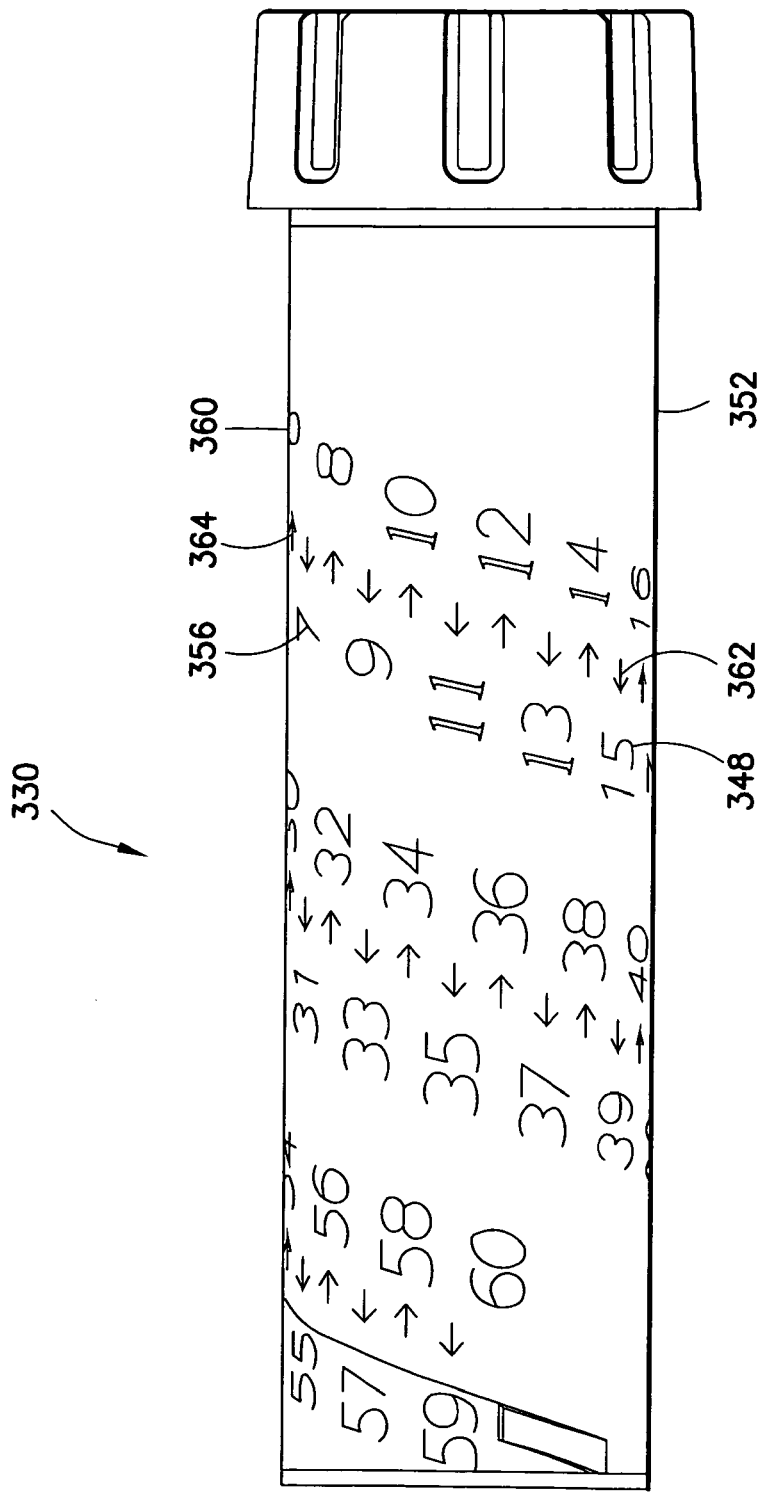
FIG. 23 is a perspective view of a DSK of the device of FIG. 21.

In another effort to decrease spacing between dosage numbers on the DSK and/or enlarge the font size and/or decrease the discrete dosage unit, FIGS. 21-23 illustrate an injection device 328 in accordance with another embodiment of the present invention. As shown in FIGS. 21 and 22, the injection device 328 includes a DSK 330 and a body 332. The body 332 includes first, second, and third dosage indicator windows 336, 340, and 344.

Similar to the previously described embodiments, dosage numbers 348 form helical patterns on a sleeve 352 of the DSK 330. Odd dosage numbers sequentially form a first substantially helical pattern 356 and even dosage numbers sequentially form a second substantially helical pattern. In contrast to the previously described embodiments, however, non-number indicators 362 form a third substantially helical pattern 364 disposed between the first and second helical patterns 356 and 360. The non-number indicators in the third helical pattern 364 alternately point to the first and second helical patterns. Thus, according to one embodiment, as shown in FIG. 22, when an even dosage number from the second helical pattern 360 is visible through the third dosage indicator window 344, a non-number indicator 362 pointing to the visible even dosage number is visible through the second dosage indicator window 340. Similarly, when an odd dosage number from the first helical pattern 356 is visible through the first dosage indicator window 336, a non-number indicator 362 pointing to the visible odd dosage number is visible through the second dosage indicator window 340.

According to another embodiment, in addition to the third helical pattern 364, the first and second helical patterns 356 and 356 also include non-number indicators, which are disposed between the dosage numbers. In such an embodiment, when a dosage number is visible through one of the three dosage indicator windows 336, 340, and 344, non-number indicators are visible through both of the remaining dosage indicator windows.

According to another embodiment, there may be four or more helical patterns arrayed on a DSK sleeve and a corresponding number of dosage indicator windows. In such an embodiment, the successive dosage numbers are visible through successive dosage indicator windows upon rotation of the DSK. According to one embodiment, when a dosage number is visible through the last dosage indicator window, upon rotation of the DSK sleeve, the next sequential dosage number becomes visible through the first dosage indicator window.

According to another embodiment, when a dosage number is visible through the last dosage indicator window, upon rotation of the DSK sleeve, the next sequential dosage number becomes visible through the next-to-last dosage indicator window. Additionally, subsequent dosage numbers become sequentially visible through ordinally lower dosage indicator windows upon rotation of the DSK sleeve. In other words, when the DSK sleeve rotates, the dosage numbers become sequentially visible through the dosage indicator windows from left to right, and then, after becoming visible through the last dosage indicator window, become sequentially visible through the dosage indicator windows from right to left.

Thus, embodiments of the present invention improve the user experience by reducing confusion and making dosage setting easier for users, particularly for visually impaired users.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of the appended claims and equivalents thereof.

The invention claimed is:
1. A medical device, comprising:
 a body for containing and dispensing a medicament, the body having a plurality of dosage indicator windows for indicating a desired dosage of medicament; and
 a dose set sleeve rotatably connected with the body for setting the desired dosage, the dose set sleeve having a plurality of dosage numbers disposed thereon;
 wherein different dosage indicator windows display different ones of the dosage numbers;
 wherein the plurality of dosage numbers and a plurality of non-number indicators are disposed on the dose set sleeve in fixed relation with one another, and the dosage numbers are arranged in parallel helical patterns on the dose set sleeve; and
 wherein the dose set sleeve and the dosage indicator windows are adapted to display one of the dosage numbers through one of the plurality of dosage indicator windows at a time, and at that time, display a non-number indicator through another of the plurality of the dosage indicator windows indicating which dosage indicator window the dosage number is displayed through.

2. The injection device according to claim 1, wherein the non-number indicator comprises an arrow.

3. The injection device according to claim 1, wherein the plurality of dosage indicator windows comprises first and second dosage indicator windows; and wherein even dosage numbers are only visible through the first dosage indicator window and odd dosage numbers are only visible through the second dosage indicator window.

4. The injection device according to claim 3, wherein the dosage numbers are arrayed on the sleeve in a pair of helical patterns, the first helical pattern comprising even numbers and the second helical pattern comprising odd numbers.

5. The injection device according to claim 4, wherein the even numbers are separated by non-number indicators and the odd numbers are separated by non-number indicators.

6. The injection device according to claim 1, wherein each of the plurality of dosage indicator windows comprises a magnifying lens.

7. The injection device according to claim 1, wherein the dose set sleeve is rotatably connected with the body to ratchet for each dosage unit; and
the dose set sleeve is connected with a knob for interfacing with a user.

8. The injection device according to claim 1, wherein the plurality of dosage indicator windows comprises first, second, and third dosage indicator windows; and
wherein even dosage numbers are only displayed through the first dosage indicator window, a non-number indicator is only displayed through the second dosage indicator window indicating which dosage indicator window a current dosage number is visible through, and odd dosage numbers are only displayed through the third dosage indicator window.

9. The injection device according to claim 1, wherein at least one of the dosage indicator windows comprises a magnifying lens.

10. A medical device, comprising:
a body for containing and dispensing a medicament, the body having a plurality of dosage indicator windows for indicating a desired dosage of medicament; and
a dose set sleeve rotatably connected with the body for setting the desired dosage, the dose set sleeve having a plurality of dosage numbers and a plurality of non-number indicators disposed thereon in fixed relation with one another, wherein the dosage numbers are arranged in parallel helical patterns on the dose set sleeve;
wherein the dose set sleeve and the dosage indicator windows are adapted to display, upon rotating the dose set sleeve to set the desired dosage, consecutive dosage numbers through alternating ones of the plurality of dosage indicator windows.

11. The injection device according to claim 10, wherein the dose set sleeve is rotatably connected with the body to ratchet for each dosage unit; and
the dose set sleeve is connected with a knob for interfacing with a user.

12. The injection device according to claim 10, wherein upon a dosage number being displayed through one of the dosage indicator windows, a non-number indicator is displayed through another one of the dosage indicator windows.

13. The injection device according to claim 12, wherein the non-number indicator is an arrow.

14. The injection device according to claim 10, wherein even dosage numbers are only displayed through the one of the dosage indicator windows and odd dosage numbers are only displayed through another one of the dosage indicator windows.

15. The injection device according to claim 14, wherein:
the plurality of dosage indicator windows comprises a pair of dosage indicator windows; and
the dosage numbers are arrayed on the dose set sleeve in a pair of helical patterns, the first helical pattern comprising even numbers and the second helical pattern comprising odd numbers.

16. The injection device according to claim 15, wherein the even numbers are separated by non-number indicators and the odd numbers are separated by non-number indicators; and
wherein upon a dosage number being displayed through one of the pair of dosage indicator windows, the non-number indicator is displayed through the remaining one of the pair of dosage indicator windows.

17. The injection device according to claim 10, wherein at least one of the dosage indicator windows comprises a magnifying lens.

18. The injection device according to claim 14, wherein the plurality of dosage indicator windows comprises first, second, and third dosage indicator windows;
wherein the plurality of dosage numbers are arrayed on the sleeve in a pair of helical patterns, the first helical pattern comprising even numbers and the second helical pattern comprising odd numbers;
wherein the plurality of non-number indicators are arrayed on the sleeve in a helical pattern; and
wherein upon a dosage number being displayed through one of the dosage indicator windows, the non-number indicator is displayed through another one of the dosage indicator windows indicating which dosage indicator window a current dosage number is displayed through.

19. A method of setting a dose for a medical device having a body and a dose set sleeve having a plurality of dosage numbers arrayed thereon in fixed relation with one another in parallel helical patterns, the method comprising:
rotating the dose set sleeve to display consecutive dosage numbers through alternating ones of a plurality of dosage indicator windows on the body.

20. The method according to claim 19, further comprising:
rotating the dose set sleeve to simultaneously display a dosage number through one of the dosage indicator windows and a non-number indicator through another one of the dosage indicator windows.

* * * * *